United States Patent
Zhou

(10) Patent No.: US 7,455,739 B2
(45) Date of Patent: Nov. 25, 2008

(54) SHAPED REINFORCING MEMBER FOR MEDICAL DEVICE AND METHOD FOR MAKING THE SAME

(75) Inventor: Pu Zhou, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 321 days.

(21) Appl. No.: 11/352,619

(22) Filed: Feb. 13, 2006

(65) Prior Publication Data

US 2006/0124212 A1  Jun. 15, 2006

Related U.S. Application Data

(63) Continuation of application No. 10/238,227, filed on Sep. 10, 2002, now abandoned.

(51) Int. Cl.
*C21D 8/00* (2006.01)
*C22F 1/18* (2006.01)

(52) U.S. Cl. .................. 148/519; 148/527; 623/1.15

(58) Field of Classification Search .................. 148/519
See application file for complete search history.

(56) References Cited

U.S. PATENT DOCUMENTS

| | | |
|---|---|---|
| 4,464,176 A | 8/1984 | Wijayarathna |
| 4,568,338 A | 2/1986 | Todd |
| 4,817,613 A | 4/1989 | Jaraczewski et al. |
| 4,840,623 A | 6/1989 | Quackenbush |
| 4,886,506 A | 12/1989 | Lovgren et al. |
| 4,898,591 A | 2/1990 | Jang et al. |
| 5,114,402 A | 5/1992 | McCoy |
| 5,290,229 A | 3/1994 | Paskar |
| 5,335,410 A | 8/1994 | Burnham |
| 5,569,218 A | 10/1996 | Berg |
| 5,603,705 A | 2/1997 | Berg |
| 5,617,854 A | 4/1997 | Munsif |
| 5,674,208 A | 10/1997 | Berg et al. |
| 5,680,873 A | 10/1997 | Berg et al. |
| 5,728,063 A | 3/1998 | Preissman et al. |
| 5,733,248 A | 3/1998 | Adam et al. |
| 5,853,400 A | 12/1998 | Samson |
| 5,860,963 A | 1/1999 | Azam et al. |
| 5,876,385 A | 3/1999 | Ikari et al. |
| 5,885,247 A | 3/1999 | Slagboom |
| 5,885,259 A | 3/1999 | Berg |
| 5,902,287 A | 5/1999 | Martin |
| 5,911,715 A | 6/1999 | Berg et al. |
| 5,935,108 A * | 8/1999 | Katoh et al. ........... 604/164.11 |
| 5,957,911 A | 9/1999 | Nesto |

(Continued)

FOREIGN PATENT DOCUMENTS

EP  0183372 A1 *  6/1986

(Continued)

*Primary Examiner*—George Wyszomierski
(74) *Attorney, Agent, or Firm*—Crompton, Seager & Tufte, LLC

(57) ABSTRACT

Medical devices, medical device components, and methods of making the same. For example, one embodiment provides a method of shaping a reinforcing member through annealing. Another exemplary embodiment includes a method of making a medical device that includes such a shaped reinforcement member incorporated therein. Yet another exemplary embodiment provides a medical device including such a shaped reinforcing member therein.

15 Claims, 3 Drawing Sheets

U.S. PATENT DOCUMENTS

| | | |
|---|---|---|
| 5,971,974 A | 10/1999 | Keisz |
| 5,980,502 A | 11/1999 | Berg |
| 5,997,526 A | 12/1999 | Giba et al. |
| 6,004,280 A | 12/1999 | Buck et al. |
| 6,039,723 A | 3/2000 | Tanaka et al. |
| 6,042,578 A | 3/2000 | Dinh et al. |
| 6,066,126 A | 5/2000 | Li et al. |
| 6,103,037 A | 8/2000 | Wilson |
| 6,159,187 A | 12/2000 | Park et al. |
| 6,171,295 B1 | 1/2001 | Garabedian et al. |
| 6,193,705 B1 | 2/2001 | Mortier et al. |
| 6,197,014 B1 | 3/2001 | Samson et al. |
| 6,212,422 B1 | 4/2001 | Berg et al. |
| 6,245,030 B1 | 6/2001 | DuBois et al. |
| 6,245,103 B1 * | 6/2001 | Stinson ............... 623/1.22 |
| 6,254,550 B1 | 7/2001 | McNamara et al. |
| 6,273,881 B1 | 8/2001 | Kiemeneij |
| 6,325,790 B1 | 12/2001 | Trotta |
| 2001/0051790 A1 | 12/2001 | Parker |

FOREIGN PATENT DOCUMENTS

| | | |
|---|---|---|
| EP | 0 278 937 | 8/1988 |
| EP | 0 812 928 | 12/1997 |

* cited by examiner

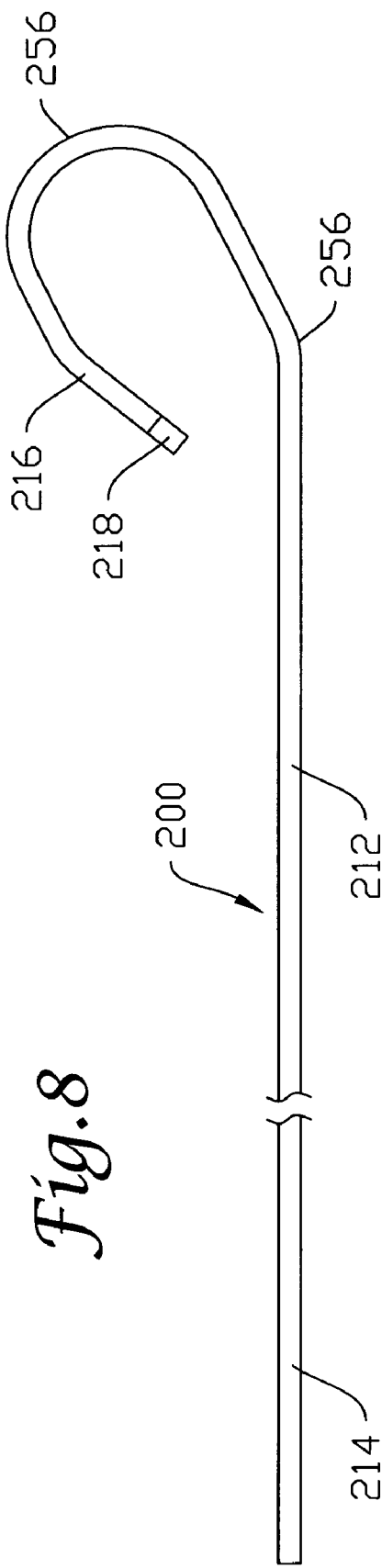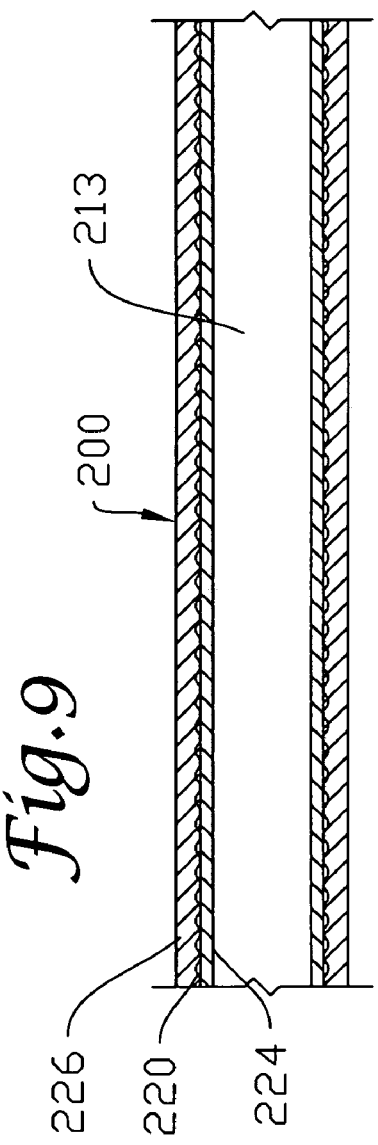

SHAPED REINFORCING MEMBER FOR MEDICAL DEVICE AND METHOD FOR MAKING THE SAME

CROSS-REFERENCE TO RELATED APPLICATIONS

This application is a continuation of U.S. patent application Ser. No. 10/238,227 filed Sep. 10, 2002, now abandonded.

FIELD OF THE INVENTION

The invention generally relates to medical devices. More specifically, the invention relates to shaped reinforcing members for medical devices, and methods for producing the same.

BACKGROUND

It is generally known to provide reinforcing members for use in intravascular catheters. It is also generally known to provide for curves or other shapes along the length of such catheters. The prior art offers a number of different structures and mechanisms for providing such curves or shapes within the body of the catheter. Each of these different structures and mechanisms has certain advantages and disadvantages. There is an ongoing need to provide alternative structures and mechanisms to provide shapes or curves in medical devices, such as catheters.

SUMMARY

The invention relates to alternative designs and methods of making medical devices. Some embodiments relate to shaping reinforcing members adapted and configured for use in medical devices. For example, one embodiment provides a method of shaping a reinforcing member adapted and configured for use in a medical device. Another exemplary embodiment includes a method of making a medical device that includes a shaped reinforcement member incorporated therein. Yet another exemplary embodiment provides a medical device including a shaped reinforcing member therein.

Some embodiments of the invention will be described in more detail in the following detailed description with reference to the drawings.

BRIEF DESCRIPTION OF THE DRAWINGS

FIG. 8 shows a partial plan overview of a catheter including a shaped reinforcing member therein and including a curve proximate the distal end; and FIG. 9 is a partial cross-sectional view of a portion of the shaft of the catheter of FIG. 8.

DETAILED DESCRIPTION OF SOME EMBODIMENTS

The following detailed description should be read with reference to the drawings in which similar elements in different drawings are numbered the same. The drawings, which are not necessarily to scale, depict illustrative embodiments and are not intended to limit the scope of the invention.

Those skilled in the art and others will recognize that the invention can be manifested in a variety of forms other than the specific embodiments described and contemplated herein. Accordingly, departures in form and detail may be made without departing from the scope and spirit of the invention.

Some example embodiments generally relate to a method for shaping a reinforcing member that is adapted and configured for use in a medical device. Such methods generally comprise providing a reinforcement member, applying a biasing force to the reinforcing member to bias the reinforcing member into a desired shape, and annealing the reinforcing member while it is maintained in the desired shape. After the annealing step, the biasing force is removed, and the reinforcing member will substantially maintain the desired shape into which it was annealed. Such a shaped reinforcing member can then be incorporated into a medical device. For example, in some embodiments, the shaped reinforcing member is incorporated into the body of a catheter, and the shaped reinforcing member will influence the final shape of the catheter body. In some embodiments, the shaped reinforcing member acts to help maintain the desired shape or curve of a medical device and increases the shape or curve retention. Such medical devices are better adapted to return to the desired shape or curved position after being biased or straightened, and also resist any force that tends to bias the shape or curve from the desired position.

Figure 1:
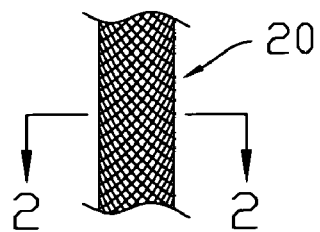
FIG. 1 is a partial side view of a reinforcing member prior to being shaped in accordance with one example embodiment.

One example embodiment is illustrated in FIGS. 1-4. FIG. 1 shows a portion of a reinforcing member 20. In this embodiment, the reinforcing member 20 comprises a reinforcing braid. Those of skill in the art and others will recognize that other reinforcing members, such as coils, tubes, wires, fabric, mesh, filaments, and combinations thereof, and other like structures for use as reinforcing structures can be used in accordance with other embodiments. The particular braided reinforcing member 20 shown is adapted and configured for use in a medical device such as a catheter, and in particular an intravascular catheter. Some examples of intravascular catheters include guide catheters, diagnostic catheters, angiographic catheters, balloon catheters, atherectomy catheters, or the like. It will also be understood that reinforcing structures adapted and configured for use in medical devices other than catheters are also contemplated.

Figure 2:
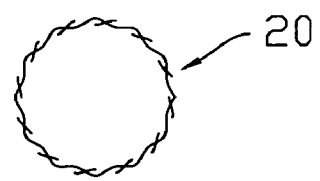
FIG. 2 is a cross-sectional view taken along line 2-2 of the reinforcing member of FIG. 1.

The reinforcing member 20 can be of any appropriate size and shape for use in the particular medical device into which it will be incorporated. As shown in FIG. 2, the reinforcing member 20 illustrated has a generally circular cross-sectional shape, and is appropriately sized for use in an intravascular catheter. A broad variety of other shapes and sizes could be used, depending upon the intended use and desired characteristics of the reinforcing member. For example, in some embodiments, the reinforcing member could have a flat, curved, oval, or multisided cross-sectional shape, for example, triangular, square, rectangular, pentagonal, hexagonal, and so fourth.

Furthermore, the reinforcing member 20 can be formed using any suitable technique for forming the appropriate reinforcing structure. In the case of a braided reinforcing member 20, the braid can be formed using any suitable technique or pattern. In some example embodiments, the patterns and techniques used can include 1 over 1, 2 over 2, 3 over 3, or the like. The braid can be formed using a suitable number of strands or filaments. The number of strands or filaments used in such a braided reinforcing member will often depend upon the desired characteristics of the braid, and the patterns or techniques used to form the braid. In some embodiments, the number of strands used can range from 16 to 32, and in some embodiments from 8 to 32. The strands or filaments should be appropriately sized and shaped depending upon the desired characteristics of the braid and pattern used. For example, in some embodiments, the braid is made using braid filaments having a thickness in the range of about 0.00025 to about 0.00225 inches, and in some embodiments, from about 0.0015 to about 0.0020 inches. In some embodiments, the cross-sectional shape of the filaments can be circular, oval, or multisided, for example, triangular, square, rectangular, pentagonal, hexagonal, and so fourth.

The resulting braid can be produced such that it is appropriately sized and shaped for use in the particular medical device into which it will be incorporated. In some embodiments, the reinforcing member is a braid having a braid density of at least about 30 pic, and in some embodiments in the range of about 60 to about 300 pic. The braid diameter in some embodiments is in the range of about 0.00025 inches to about 0.00225 inches, and in some embodiments, in the range of about 0.0015 to about 0.005 inches. The braid length in some embodiments is in the range of about 20 inches to about 60 inches, and in some embodiments, in the range of about 31.5 inches to about 47.25 inches.

At least a portion of the reinforcing member 20, or at least some of the filaments or strands making up the reinforcing member 20, can be made of a metallic material, polymeric material, or combinations thereof. Suitable metallic materials include those that can be annealed into a desired shape. Some examples of metallic materials include stainless steel, tungsten, nickel, cobalt, titanium, gold, iridium, or alloys thereof, or other such metallic materials, or combinations thereof. Some particular examples of suitable stainless steel alloys include 304 and 440A and 440C stainless steel alloys. In some particular example embodiments, the reinforcing member is a reinforcing braid adapted and configured for use in an intravascular catheter and is formed with primarily stainless steel filaments. In some embodiments, the reinforcing member 20 includes combinations of filaments or strands made up of different types of materials. For example, in some particular example embodiments, the reinforcing member 20 is a reinforcing braid formed with a combination of stainless steel filaments and tungsten filaments.

Suitable polymeric materials also include those that can be annealed into a desired shape. Some examples of suitable polymers include nylon, polyesters, acrylics and combinations of mixtures thereof.

Figure 3:
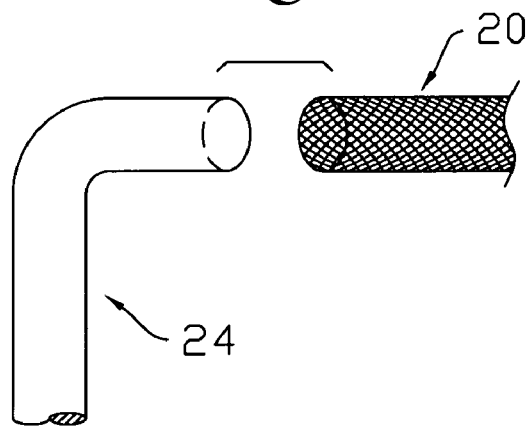
FIG. 3 is a partial side view of the reinforcing member of FIG. 1 being inserted onto a mandrel in accordance with one example embodiment.
Figure 4:
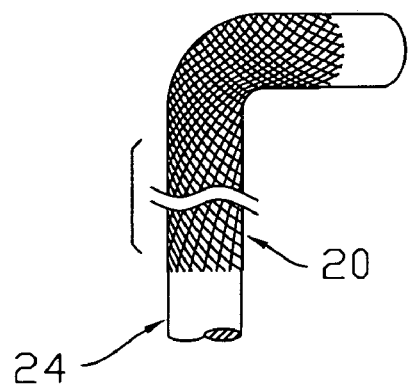
FIG. 4 is a partial side view of the reinforcing member of FIG. 1 mounted onto the mandrel.

As discussed above, a biasing force is applied to the reinforcing member 20 to bias the reinforcing member 20 into a desired shape. It will be understood by those of skill in the art and others that any of a broad variety of techniques or structures can be used to bias the reinforcing member into the desired shape. As shown in FIG. 3, in this particular embodiment, the biasing force is applied to the reinforcing member 20 by inserting the reinforcing member 20 onto a shaped mandrel 24. As shown in FIG. 4, the mandrel 24 biases the reinforcing member 20 into a desired shape, and maintains the reinforcing member 20 in the desired shape. The mandrel can be made of any suitable material that can maintain the reinforcing member 20 in the desired shape, and can generally withstand the annealing temperatures used in the particular embodiment, as discussed below.

The reinforcing member 20 is then annealed while being held in the desired shape by the biasing member 24. As used herein, the term "anneal" means to heat treat the material of the reinforcing member at a specified temperature for a specific length of time to remove internal strains resulting from previous operations. The annealing step is therefore preformed by heating the reinforcing member 20 to an annealing temperature while it is in the desired shape, and maintaining the reinforcing member at the annealing temperature for a specified period of time. The time and temperature needed to anneal the reinforcing member 20 into the desired shape is highly dependent upon the material that is used to make the reinforcing member 20. Those of skill in the art and others will be able to easily determine the requisite annealing times and temperatures for different types of materials through general knowledge of material sciences known in the art. The appropriate annealing time and temperature should allow for proper annealing of the reinforcing member such that the desired shape is maintained, but not to significantly harm the physical construction of the reinforcing member. Additionally, in some embodiments, the annealing is performed at an appropriate annealing time and temperature such that no significant amount of hardening occurs to the material making up the reinforcing member 20. In some other embodiments, some hardening is acceptable.

For example, when the reinforcing member is a braid configured primarily of elongated filaments of stainless steel, the annealing temperature in some embodiments is in the range of about 500° F. to about 1000° F. and the annealing time for some such embodiments is in the range of about 0.25 to about 5 hours. In some embodiments, the annealing temperature is in the range of about 600° F. to about 900° F. and the annealing time for some such embodiments is in the range of about 0.5 to about 4 hours.

For another example, when the reinforcing member is a braid made up primarily of elongated polymer filaments, the annealing temperature in some embodiments is in the range of about 280° F. to about 370° F. and the annealing time for some such embodiments is in the range of about 0.1 to about 2 hours. In some embodiments, the annealing temperature is in the range of about 300° F. to about 420° F. and the annealing time for some such embodiments is in the range of about 0.1 to about 2 hours.

After the annealing process or step, the reinforcing member 20 is removed from the biasing member 24. Due to the annealing step, the reinforcing member 20 will substantially maintain the desired shape. The reinforcing member 20 can then be incorporated into a medical device. For example, the reinforcing member 20 can be thereafter incorporated into the body of a catheter, such as an intravascular catheter.

Figure 5:
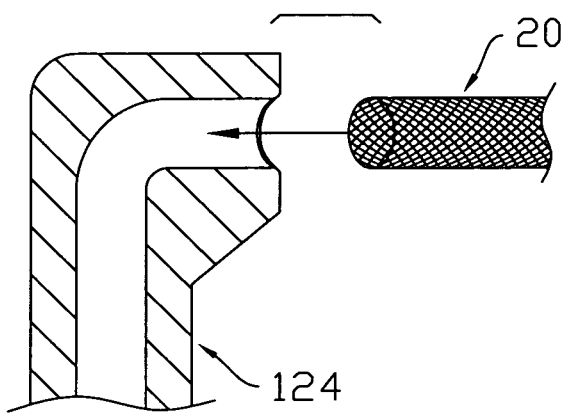
FIG. 5 is a partial cross-sectional side view of the reinforcing member of FIG. 1 being inserted into a jig in accordance with another exemplary embodiment.
Figure 6:
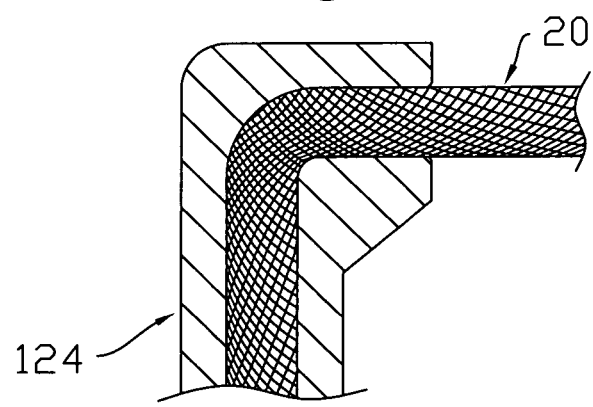
FIG. 6 is a partial cross-sectional side view of the reinforcing member of FIG. 5 inserted into the jig.
Figure 7:
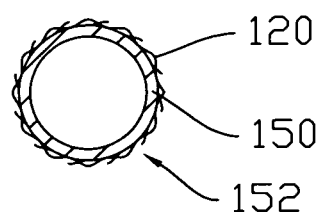
FIG. 7 is a cross-sectional view of an alternative reinforcing member showing the reinforcing member disposed around an inner layer.

FIGS. 5 and 6 show another example embodiment wherein the method is similar to that of the embodiment depicted in FIGS. 1-4, but the biasing force is applied to the reinforcing member 20 by insertion of the reinforcing member 20 into a shaped jig 124. As shown in FIG. 6, the reinforcing member 20 is maintained within the jig 124 and conforms to a desired shape. After the reinforcing member 20 is inserted into the jig 124, the annealing step is performed while the reinforcing member 20 is maintained in the desired shape. After the annealing step, the reinforcing member 20 is removed from the shaped jig 124. Due to the annealing step, the reinforcing member 20 substantially maintains the desired shape when removed from the shaped jig 124.

In some embodiments, it is also contemplated that prior to the annealing step, the reinforcing member can be incorporated with at least another component or portion of the medical device. For example, referring now to FIG. 8, a reinforcing member 120 could be disposed or formed over an inner tubular member 150 prior to shaping of the reinforcing member 120 through annealing in accordance with the same general method as discussed above. FIG. 8 shows a cross-sectional view of a reinforcing member 120, wherein the reinforcing member 120 has been disposed around an inner tubular member or layer 150 to form a tubular assembly 152. In some such embodiments, for example where the final medical device will be a catheter, the inner tubular layer 150 can be made of a lubricious material, for example tetrafluoroethylene (PTFE), or a copolymer of tetrafluoroethylene with perfluoroalkyl vinyl ether (PFA) (more specifically, perfluoropropyl vinyl ether or perfluoromethyl vinyl ether), or the like. The tubular assembly 152, including both the inner tubular member 150 and the reinforcing member 120 would be biased into a desired shape, and then annealed using the same general methodology as discussed above. The annealing step would anneal the reinforcing member 120 such that the reinforcing member 120 would maintain the desired shape. The tubular assembly 152 could thereafter be incorporated into a finished catheter.

As discussed above, the shaped reinforcing members, or tubular assemblies including a shaped reinforcing member, can be incorporated into medical devices. For example, a shaped reinforcing member could be incorporated into a catheter 200 as shown in FIGS. 8 and 9. For purposes of illustration only, catheter 200 is depicted in FIGS. 8 and 9 as an intravascular catheter, and in particular, an intravascular guide catheter. However, it can be appreciated that catheter 200 can be any one of multiple different intravascular or non-intravascular catheter types. A person of ordinary skill in the art will be familiar with different types of catheters appropriate for multiple embodiments. Some examples of other intravascular catheters include, but are not limited to, diagnostic catheters, balloon catheters, atherectomy catheters, stent delivery catheters, and the like. Moreover, although discussed with specific reference to catheters, the invention can be applicable to almost any medical device having a reinforcing member. For example, the shaped reinforcing member construction and methodology is contemplated for use with medical devices such as guidewires, intravascular rotational devices, or the like.

FIGS. 8 and 9 show a catheter 200 incorporating a reinforcing member 220 (FIG. 9) therein that has been shaped in accordance with the general method of shaping a reinforcing member as disclosed herein. Referring to FIG. 8, the catheter 200 includes a generally elongated shaft 212 having a proximal portion 214 and a distal portion 216. A distal tip 218 is disposed at the distal end of the distal portion 216. The reinforcing member 220 can extend the entire length of the shaft 212, or can extend through only a portion or portions of the shaft 212. Additionally, the reinforcing member 220 can end prior to the distal tip 218, can extend into a portion of the tip 218, or can extend the entire length of the tip 218.

The catheter shaft 212 can be manufactured, include structure, and be made of materials so as to provide the desired characteristics of the catheter 200, depending upon the intended use. For example, the shaft 212 can be manufactured using structure and materials so as to maintain a desired level of flexibility and torquability appropriate for maneuvering the catheter 200 as desired, for example, through the vasculature of a patient. In some embodiments, the catheter 200 can include a shaft 212 that is generally characterized as having a tubular member construction that includes at least a single lumen 213 (FIG. 9) extending the length of shaft 212. The lumen 213 within the shaft 212 can possess an inner diameter capable of transmitting fluids, or in some cases, receiving another medical device, such as a guidewire or another catheter, for example, a diagnostic catheter, a balloon catheter, a stent delivery catheter, or the like. In some embodiments, the lumen within shaft 212 is adapted and configured to accommodate another medical device having outer diameters in the range of 5F-10F.

The shaft 212 including the reinforcing layer 220 can have one or more additional layers in addition to the reinforcing layer 220. For example, in the embodiment shown in FIG. 9, which is a partial cross-sectional view of a portion of the shaft 212, the shaft 212 can have a three layer tubular construction including an inner tubular layer 224, the reinforcing layer 220 disposed about the inner tubular layer 224, and an outer tubular layer 226 disposed about the reinforcing layer 220. The inner tubular layer 224 defines an inner lumen 213, as generally described above.

The additional layers of the shaft 212, for example, the inner tubular layer 224 and the outer tubular layer 226 can be manufactured from any suitable material to impart the desired characteristics. Examples of some suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. One example of a suitable polyoxymethylene (POM) is Delrin™ commercially available from Dow Chemicals.

In some such embodiments, the inner tubular layer 224 can be made of a lubricious material, for example tetrafluoroethylene (PTFE), or a copolymer of tetrafluoroethylene with perfluoroalkyl vinyl ether (PFA) (more specifically, perfluoropropyl vinyl ether or perfluoromethyl vinyl ether), or the like.

The outer layer 226 or layers can be made up of one or more outer tubular segments disposed over the reinforcing layer 220, and can be constructed with any suitable materials and structures to impart the desired characteristics to the shaft. For example, the outer layer 226 can comprise any of the materials listed above, and in some particular embodiments can include nylon, polyether block amide (PEBA), or a blend of the two and in some embodiments can have a durometer on the order of about 5-90D. The material of outer layer 226 can be blended with a liquid crystal polymer (LCP). For example, the mixture can contain up to about 6% LCP. This has been found to enhance torqueability. The outer layer 226 can be made up of a plurality of outer tubular segments disposed along the shaft 212, each segment being made of materials having different durameters to impart varying degrees of flexibility to different sections of the shaft.

The shaft can be constructed using any appropriate technique, for example, by extrusion, a heat bonding process, molding, and the like.

Some other examples of suitable catheter shaft constructions and materials can be found in U.S. Pat. Nos. 5,569,218; 5,603,705; 5,674,208; 5,680,873; 5,733,248; 5,853,400; 5,860,963; and 5,911,715, all of which are incorporated herein by reference.

The catheter 200 can be curved or shaped as desired utilizing the shaped reinforcing member 220. For example, catheters, such as guide catheters, can include a variety of shapes specific for different bodily passages and procedures. The stabilization of a catheter's position within a patient's anatomy is often achieved through curves or bends 256 imparted into shaft 212 at least partially by the shaped reinforcing member. These pre-formed curves 256 act by anchoring a selected portion of shaft 212 against an opposing wall within a patient's vasculature or other body portion. Proper anchoring is often achieved by matching the predisposed shape of the curved shaft 212 with the general curved anatomical shape around a targeted site. In vascular procedures involving treatment to one of the coronary arteries, often a curve is imparted proximate the distal portion 216 of shaft 212 with the intention of placing the catheter's distal tip 218 at a desired angle. In embodiments of catheter 200 that are designed for a procedure in a coronary artery, for example, shaft 212 can be shaped so that when it is inserted through the aorta of the patient, the curvature of shaft 212 will place distal tip 218 at an angle that engages one of the coronary ostia. Those of skill in the art recognize some different shapes by names such as Judkins Right, Judkins Left, Amplatz Right, Amplatz Left, Bentson, Shepherd Hook, Cobra, Headhunter, Sidewinder, Newton, Sones and others, each formed in a different shape.

As can be seen, a broad variety of shapes and curves can be formed and maintained using reinforcing members that are annealed to maintain such shapes. In at least some embodiments, one of the advantages of annealing the reinforcing members to maintain these curved shapes is that it increases the curve retention and curve support of the medical device, such as a catheter, into which such reinforcing members are incorporated. Such catheters are better adapted to come back to the curved position after being biased or straightened, and also resist any force that tends to open the curves to a wider angle.

Having thus described some example embodiments of the invention, those of skill in the art will readily appreciate that other embodiments may be made and used within the scope of the invention. Numerous advantages of the invention covered by this document have been set forth in the foregoing description. It will be understood, however, that this disclosure is, in many respects, only illustrative. Changes can be made in details, particularly in the manner of size, shape, and arrangement of parts without exceeding the scope of the invention. Additionally, changes can be made in details with regard to order of steps and performing methods and other arrangements in accordance with the invention. The invention's scope is, of course, defined in the language of the claims.

What is claimed is:

1. A method for manufacturing a medical device, the method comprising:
    providing a reinforcing member consisting essentially of stainless steel, tungsten or combinations thereof;
    applying a biasing force to the reinforcing member to bias the reinforcing member into a desired shape that includes a curve;
    annealing the reinforcing member;
    removing the biasing force, wherein the reinforcing member substantially maintains the desired shape when the biasing force is removed; and
    disposing a tubular member on the reinforcing member, wherein the reinforcing member substantially maintains the desired shape when the tubular member is disposed on the reinforcing member such that the finished medical device maintains the desired shape.

2. The method according to claim 1, wherein providing a reinforcing member includes providing a reinforcing braid.

3. The method according to claim 1, wherein annealing the reinforcing member includes heating the reinforcing member at a temperature in the range of about 500° F. to about 1000° F.

4. The method according to claim 1, wherein annealing the reinforcing member is performed over a time period in the range of about 0.25 to about 5 hours.

5. The method according to claim 1, wherein annealing the reinforcing member includes removing internal strains in the reinforcing member caused by applying the biasing force to bias the reinforcing member into the desired shape.

6. The method according to claim 1, wherein applying a biasing force to the reinforcing member to bias the reinforcing member into a desired shape that includes a curve includes loading the reinforcing member onto a mandrel.

7. The method according to claim 1, wherein applying a biasing force to the reinforcing member to bias the reinforcing member into a desired shape that includes a curve includes loading the reinforcing member into a jig.

8. The method according to claim 1, wherein the reinforcing member includes a proximal portion and a distal portion, and wherein the desired shape of the reinforcing member includes one or more curves formed in the distal portion.

9. The method according to claim 1, further comprising disposing the reinforcing member about an inner tubular member.

10. A method for manufacturing a catheter, the method comprising:
    providing a reinforcing member consisting essentially of stainless steel, tungsten or combinations thereof;
    forming a curve in the reinforcing member;
    annealing the reinforcing member;
    disposing the annealed reinforcing member on a first tubular member; and
    disposing a second tubular member on the annealed reinforcing member, wherein the curve formed in the annealed reinforcing member substantially maintains its shape when the second member is disposed on the annealed reinforcing member such that the finished catheter substantially maintains a desired shape.

11. The method according to claim 10, wherein providing a reinforcing member includes providing a reinforcing braid.

12. The method according to claim 10, wherein annealing the reinforcing member includes heating the reinforcing member at a temperature in the range of about 500° F. to about 1000° F.

13. The method according to claim 10, wherein annealing the reinforcing member is performed over a time period in the range of about 0.25 to about 5 hours.

14. The method according to claim 10, wherein annealing the reinforcing member includes removing internal strains in the reinforcing member caused by forming the curve in the reinforcing member.

15. A method for manufacturing a catheter, the method comprising:
    providing a tubular reinforcing braid consisting essentially of stainless steel, tungsten or combinations thereof;

forming a curve in the tubular reinforcing braid;
annealing the tubular reinforcing braid;
disposing the annealed tubular reinforcing braid on a first tubular member; and
disposing a second tubular member on the annealed tubular reinforcing braid, wherein the curve formed in the annealed tubular reinforcing braid substantially maintains its shape when the second member is disposed on the annealed tubular reinforcing braid such that the finished catheter substantially maintains a desired shape.

* * * * *